United States Patent
Kirkin et al.

(10) Patent No.: US 9,567,567 B2
(45) Date of Patent: Feb. 14, 2017

(54) COMPOSITIONS AND METHODS FOR PRODUCING DENDRITIC CELLS

(75) Inventors: Alexei Kirkin, Copenhagen (DK); Karine Djandjougazian, Copenhagen (DK); Martin Roland Jensen, Holte (DK)

(73) Assignee: Cytovac A/S, Horsholm (DK)

( * ) Notice: Subject to any disclaimer, the term of this patent is extended or adjusted under 35 U.S.C. 154(b) by 534 days.

(21) Appl. No.: 13/816,359

(22) PCT Filed: Aug. 11, 2011

(86) PCT No.: PCT/EP2011/063867
§ 371 (c)(1),
(2), (4) Date: Apr. 25, 2013

(87) PCT Pub. No.: WO2012/020100
PCT Pub. Date: Feb. 16, 2012

(65) Prior Publication Data
US 2013/0216584 A1    Aug. 22, 2013

(30) Foreign Application Priority Data

Aug. 11, 2010 (GB) .................................. 1013443.5

(51) Int. Cl.
| | |
|---|---|
| *C12N 5/0784* | (2010.01) |
| *C12N 5/0783* | (2010.01) |
| *A61K 35/15* | (2015.01) |
| *A61K 35/17* | (2015.01) |
| *A61K 39/00* | (2006.01) |
| *A61K 35/12* | (2015.01) |

(52) U.S. Cl.
CPC ............ *C12N 5/0639* (2013.01); *A61K 35/15* (2013.01); *A61K 35/17* (2013.01); *A61K 39/0011* (2013.01); *C12N 5/0638* (2013.01); *A61K 2035/124* (2013.01); *A61K 2039/5154* (2013.01); *A61K 2039/5158* (2013.01); *C12N 2500/90* (2013.01); *C12N 2501/02* (2013.01); *C12N 2501/2301* (2013.01); *C12N 2501/2306* (2013.01); *C12N 2501/25* (2013.01); *C12N 2501/91* (2013.01); *C12N 2506/115* (2013.01); *C12N 2533/70* (2013.01); *C12N 2533/90* (2013.01)

(58) Field of Classification Search
None
See application file for complete search history.

(56) References Cited

U.S. PATENT DOCUMENTS 6,498,034 B1    12/2002    Strobl

FOREIGN PATENT DOCUMENTS

| JP | 2009-013166 | | 1/2009 |
|---|---|---|---|
| JP | 2009-065835 | | 4/2009 |
| WO | WO 98/06826 | | 2/1998 |
| WO | WO 98/23728 | | 6/1998 |
| WO | WO03/045427 | * | 6/2003 |
| WO | WO2006/033991 | * | 3/2006 |

OTHER PUBLICATIONS

Mackensen et al (Journal of Clinical Oncology, 2006, vol. 24, pp. 5060-5069).*
Bachman et al (Journal of Immunology, 2005, vol. 175, pp. 4677-4685).*
Efferson et al (Anticancer Research, 2005, vol. 25, pp. 715-724).*
Wheeler (Salud p'ublica de M'exico, 1997, vol. 4, pp. 283-287).*
The abstract of Tanigawa et al (Journal of Immunotherapy, 2008, vol. 31, p. 926).*
Dumortier et al (Journal of Immunology, 2005, vol. 175, pp. 855-863).*
Klebanoff et al (PNAS, 2005, vol. 102, pp. 9571-9576).*
Vuillier et al "Functional Monocyte-Derived Dendritic Cells can be Generated in Chronic Lymphocytic Leukaemia" British Journal of Haemotology vol. 115, pp. 831-844. 2001.
Xia et al "Heparin Induces Differentiation of CD1a+ Dendritic Cells from Monocytes: Phenotypic and Functional Characterization" The Journal of Immunology vol. 168, pp. 1131-1138. 2002.
Lehner et al "Functional Characterization of Monocyte-Derived Dendritic Cells Generated Under Serumfree Culture Conditions" Immunology Letters vol. 99, pp. 209-216. 2005.
Hildenbrand et al "IFN-y Enhances $T_H1$ Polarisation of Monocyte-Derived Dendritic Cells Matured with Clinical-Grade Cytokines Using Serum-Free Conditions" Anticancer Research vol. 28, pp. 1467-1476. 2008.

* cited by examiner

*Primary Examiner* — Karen Canella
(74) *Attorney, Agent, or Firm* — Cesari and McKenna LLP

(57) ABSTRACT

The present invention relates to compositions and methods for producing dendritic cells and particularly to compositions and methods for producing immature dendritic cells that are immunocompetent. We describe a method of producing dendritic cells by cultivation of monocytes, characterised by at least one of: pre-treatment of a tissue culture surface with at least one of: a substantially plasma-free and serum-free pre-treatment medium, a pre-treatment medium comprising heparin, and a pre-treatment medium comprising a protein solution; adsorption of monocytes using at least one of: a substantially plasma-free and serum-free adsorption medium; cultivation of monocytes using a substantially plasma-free and serum-free cultivation medium. We also describe compositions including the dentritic cells and uses of the dentritic cells.

15 Claims, 13 Drawing Sheets

RT-PCR analysis of IL-15(A) and GAPDH (B) expression in DC.
Samples of DC lysates (lanes 1-10), control without RT (lane 11), control in the absence of cDNA (lane 12 A).
The last lane - 100bp ladder.

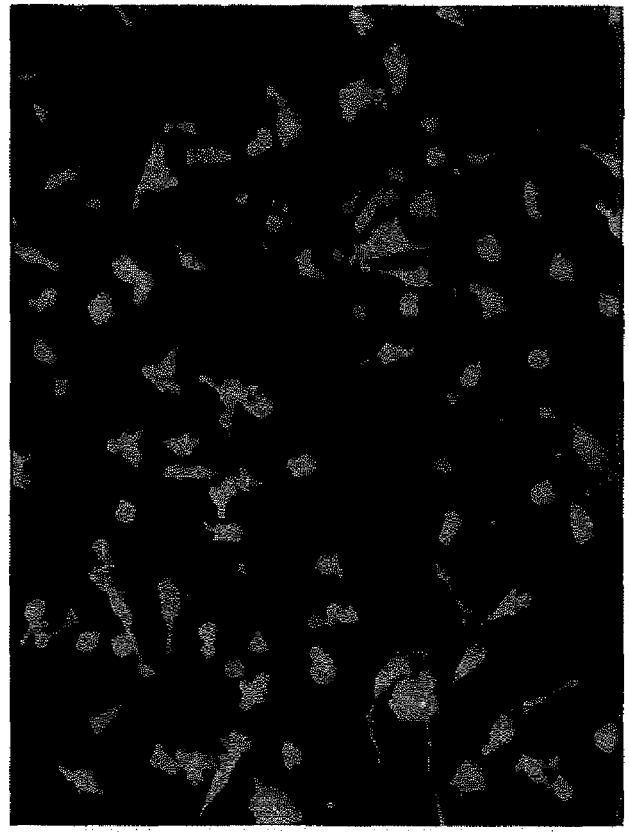
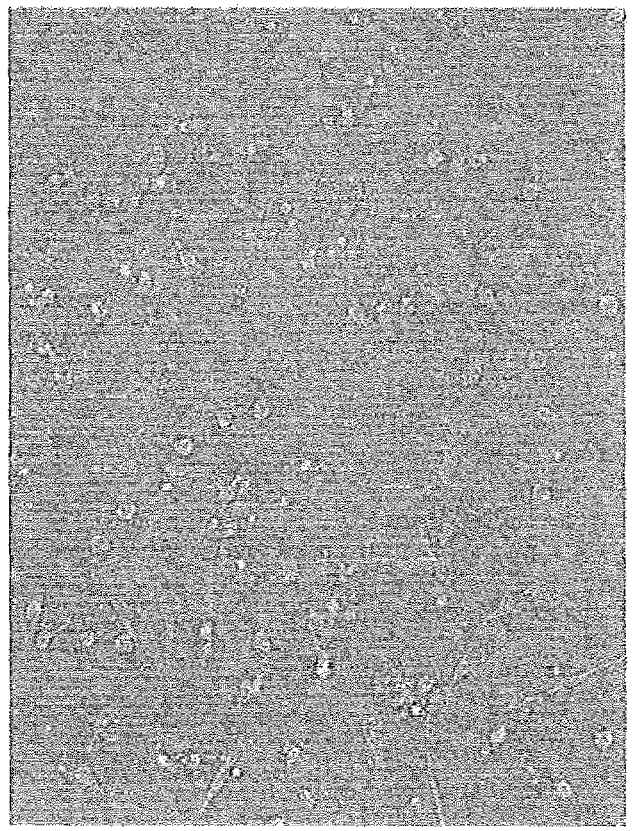
Figure 10

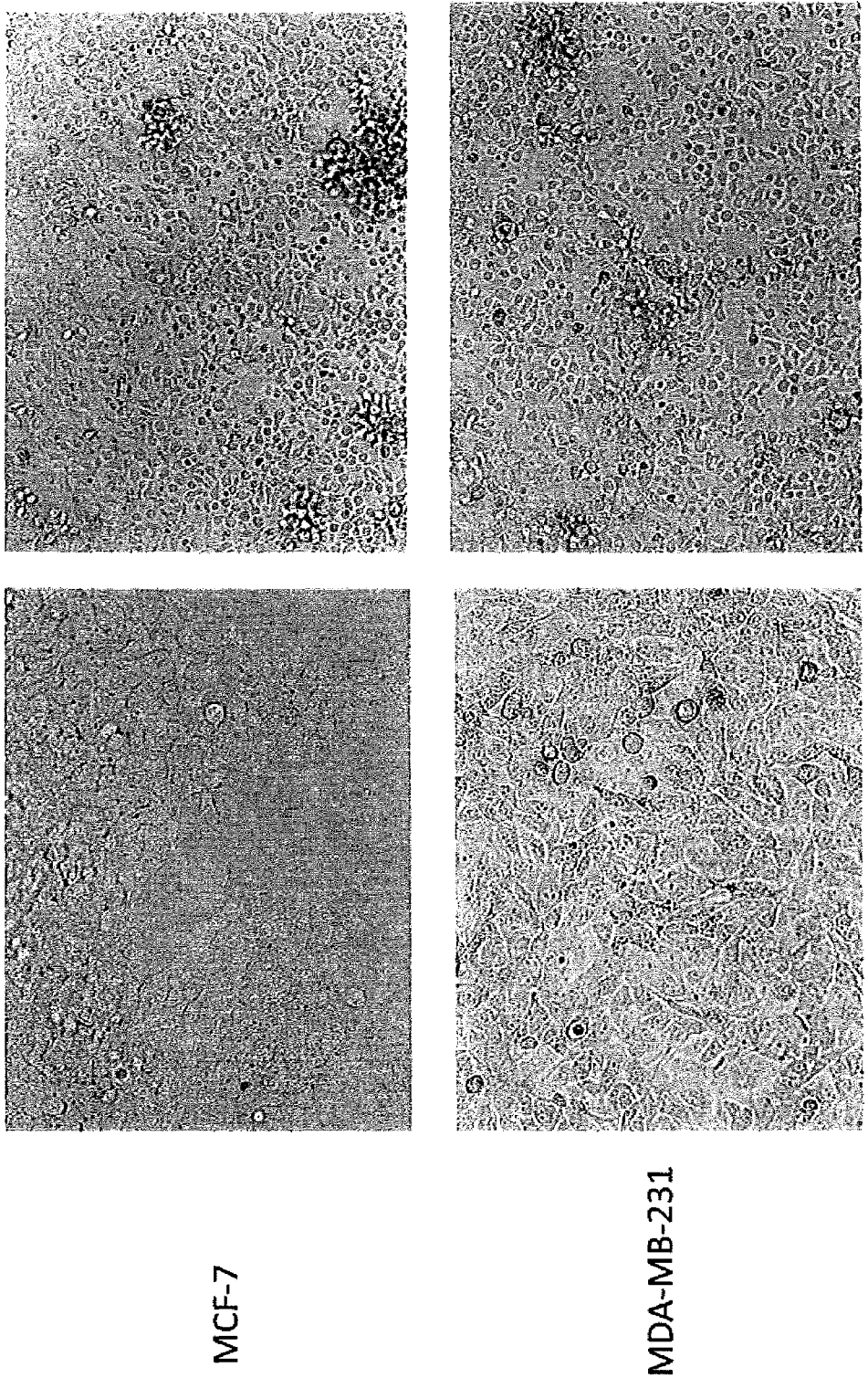

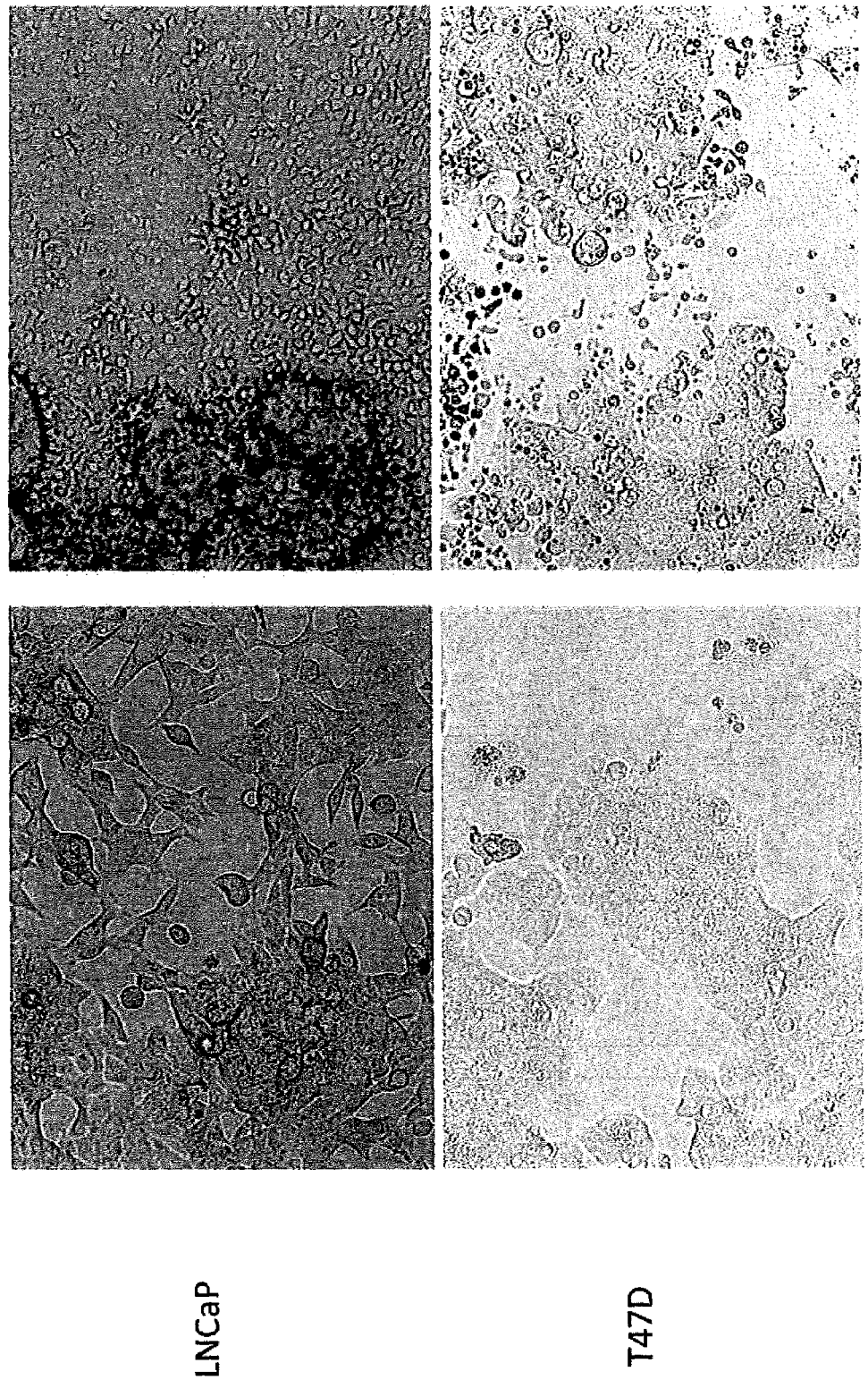

COMPOSITIONS AND METHODS FOR PRODUCING DENDRITIC CELLS

This application is the national phase under 35 USC 371 of international application no. PCT/EP2011/063867, filed Aug. 11, 2011, which claims the benefit of the priority date of Great Britain Application No. 1013443.5 Aug. 11, 2010, The contents of the aforementioned applications are incorporated herein in their entirety.

The present invention relates to compositions and methods for producing dendritic cells and particularly to compositions and methods for producing immature dendritic cells that are immunocompetent.

Tumour cells, similar to many infectious agents, express specific protein antigens that are absent in normal cells. Potentially, the immune system is able to recognize these tumour cells as foreign and eliminate them. The major effector cell population able to mediate tumour cell recognition and destruction is cytotoxic T lymphocytes (CTL). In order to induce a CTL response, the antigens should be presented to CTL precursors by antigen-presenting cells (APC). During the last 15 to 20 years, immunotherapy research has focussed on the use of dendritic cells as the most efficient antigen-presenting cells (References 1 and 2).

The most convenient source for preparation of dendritic cells is blood monocytes. Peters described the ability of monocytes to transform, in culture, into dendritic cell-like cells, both spontaneously (3) and in the presence of two cytokines (Granulocyte Macrophage Colony-Stimulating Factor (GM-CSF) and Interleukin-4 (IL-4)) (4). Following research by Romani et al., (1994) (5) and Sallusto and Lanzavecchia (1994) (6), monocytes cultured in the presence of GM-CSF and IL-4 became the most widely-used source for dendritic cell preparation. Preparation of dendritic cells from monocytes is traditionally carried out in the presence of fetal calf serum (FCS). FCS is currently not recommended for use in the preparation of compositions for immunotherapy since the patient risks development of type 1 hypersensitivity to bovine serum albumin (BSA) (10).

There are two types of dendritic cells—mature and immature. Mature dendritic cells can be characterised by the presence of CD83, which is a well known marker of mature dendritic cells (18). Immature dendritic cells can be identified by expression of CD1a and CD4, which are characteristic markers for immature dendritic cells. The immature state of dendritic cells is their natural state in an organism. After appearance of an infection or diseased cells, dendritic cells will localize in the effected organs or tissue and phagocytize the infected agents or diseased cells. They will then migrate to regional lymph nodes to present the processed antigens to antigen-specific T lymphocytes. During the process of migration, and probably during initial interaction with antigen-specific T cells, dendritic cell maturation is initiated, leading to increased T-cell stimulatory activity. The common conception is that, to be effective antigen-presenting cells, dendritic cells should be mature, since mature dendritic cells (DC) express high levels of co-stimulatory molecules, such as CD80 and CD86, and are better able to migrate than immature DC.

There are, however, some studies demonstrating that immunization with immature dendritic cells might have a clinical effect. A recent review of the use of dendritic cells for treatment of melanoma patients (11) illustrates examples where immature dendritic cells effectively elicit an immune response, indicating their potential immunocompetence. In fact, the clinical effects demonstrated in one of the first studies of dendritic cell-based immunotherapy of melanoma patients were obtained using immature dendritic cells (9).

Use of immature DC as antigen-presenting cells has potential advantages, compared with use of mature DC. Mature dendritic cells stimulate lymphocytes in an antigen-nonspecific way (see, for example, WO 2008/081035)—possibly as a result of high levels of expression of co-stimulatory molecules by fully mature DC. It has also been demonstrated that, whereas mature dendritic cells induce a strong CTL response, immature dendritic cells induce a strong central memory T cell response (12), i.e., immature DC preferentially stimulate a memory-type immune response. Induction of a memory-type immune response is important in inducing effective anti-tumour immunity because memory cells have the ability to re-circulate (due to the presence of adhesion molecules such as CD62L (13)), to be activated after initial contact with tumour cells, and to proliferate after destroying tumour cells (14, 15).

The present invention seeks to provide a method of generating immunocompetent immature DC, which show similar properties to the immature DC found in vivo. A particular problem the present invention seeks to address is to reduce or eliminate foreign body reactions during the preparation of immature DC. The present invention also aims to provide a method of generating clinically-useful and pharmaceutically-relevant immature DC. In this regard, the present invention seeks to generate dendritic cells that have the same properties as DC produced using FCS, but without using FCS in the preparation procedure.

In its broadest aspect, the present invention provides a method of producing immature dendritic cells, particularly immunocompetent immature dendritic cells, which are able to stimulate a memory-type anti-tumour T cell response. In another aspect, the present invention provides a method of producing dendritic cells that express IL-15.

According to the present invention, there is provided a method of producing dendritic cells by cultivation of monocytes, characterised by at least one of: pre-treatment of a tissue culture surface with at least one of: a substantially plasma-free pre-treatment medium, a pre-treatment medium comprising heparin, and a pre-treatment medium comprising a protein solution; adsorption of monocytes using at least one of: a substantially plasma-free adsorption medium, and a substantially serum-free adsorption medium; and cultivation of monocytes using a substantially plasma-free cultivation medium.

Preferably, the protein solution comprises human serum. Suitably, the human serum has a concentration of between 2 and 10%.

In one embodiment, the pre-treatment medium has a heparin concentration of between 10 and 200 U/ml. Ideally, the pre-treatment medium has a heparin concentration of between 25 and 100 U/ml.

In one aspect, there is provided a composition comprising dendritic cells produced in accordance with the methods described above. In one embodiment, the composition is injectable directly into a tumour.

In another aspect, the present invention provides use of immature dendritic cells produced in accordance with the methods described above for preparation of a pharmaceutical composition for treating cancer by immunotherapy.

A method of treating or preventing cancer by administering a vaccine comprising immature dendritic cells produced in accordance with the methods described above forms another aspect of the present invention. In one embodiment, the method comprises injecting the vaccine directly into a tumour.

One aspect of the present invention provides a composition comprising immature dendritic cells produced in accordance with the methods described above for treatment of cancer by immunotherapy.

A further aspect provides an antigen-presenting composition produced from immature dendritic cells produced in accordance with the methods described above.

Further aspects of the present invention include:
- a method of preparing a cytotoxic composition, comprising using an antigen-presenting composition as described above to activate T cell lymphocytes, thereby obtaining a cytotoxic composition containing tumour-specific CD8+ cytotoxic T lymphocytes;
- a method of treating cancer by stimulating an immune response against tumours, comprising administering an antigen-presenting composition as described above to a cancer patient to stimulate an immune response to the tumour antigens;
- a method of treating cancer by adoptive T cell therapy, comprising preparing a cytotoxic composition in accordance with the method described above, and administering the cytotoxic composition to a cancer patient;
- use of a dendritic cell composition as described above as antigen presenting cells for activation of cytotoxic T lymphocytes; and
- use of tumour-specific CD8+ cytotoxic T lymphocytes obtained by the method described above for preparation of a pharmaceutical composition for adoptive T cell immunotherapy.

The above and other aspects of the present invention will now be described in further detail, by way of example only, with reference to the accompanying figures and examples, in which:

FIG. 10 illustrates uptake of labelled lysate;

FIG. 12 illustrates the cytotoxic activity of the generated immune lymphocytes of HLA-A2-positive donor on HLA-A2-positive tumour cell lines MCF-7 and MDA-MB-231; and FIG. 13 illustrates the cytotoxic activity of the generated immune lymphocytes of HLA-A2-positive donor on HLA-A2-positive tumour cell line LNCaP and HLA-A2-negative cell line T47D.

Figure 1:
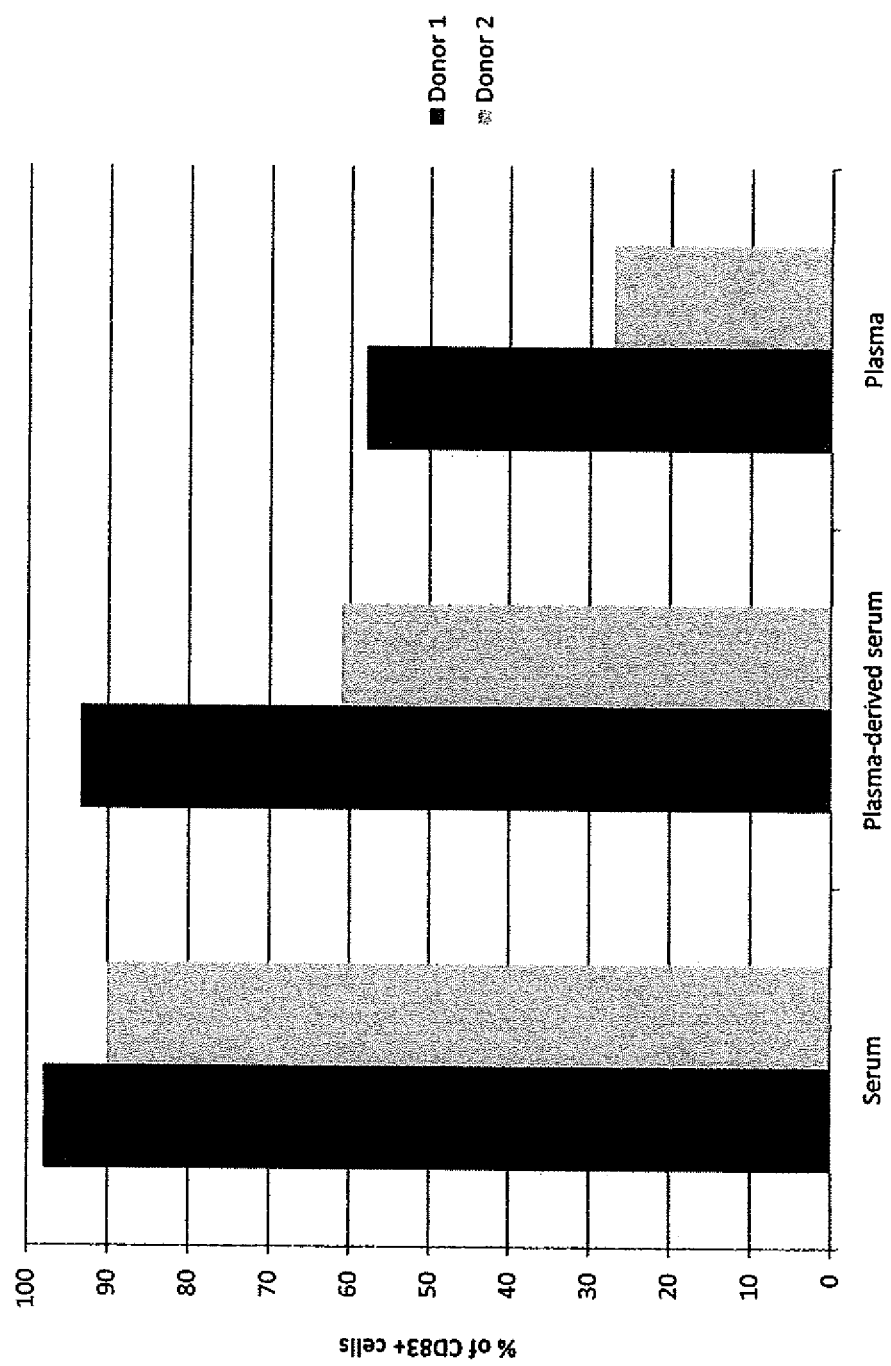
FIG. 1 illustrates the effect of inclusion of plasma in the plastic pre-treatment medium on phenotype of mature dendritic cells generated.

The procedure of the present invention for generation of dendritic cells provides significant improvements to a well-known method of generating DC from monocytes. This well-known method comprises isolation of monocytes from peripheral blood, followed by culture of the isolated monocytes in the presence of GM-CSF and IL-4 for 5-7 days. The improvements of the present invention generate advantageous properties in the dendritic cells, such as low levels of co-stimulatory molecules and high endocytic activity. The properties of immunocompetent immature dendritic cells made according to the preparation procedures of the present invention are similar to the properties of immature dendritic cells in vivo. The key properties of immature DC in vivo are: high endocytic activity, the ability to produce Interleukin-15 (IL-15), the ability to differentiate into fully mature non-exhausted dendritic cells upon addition of an appropriate maturation agent, and the ability to induce, in vitro, a memory-type antigen-specific CTL response.

To isolate monocytes from a population of mononuclear cells, obtained by centrifugation of peripheral blood, a plastic surface is commonly used to adsorb the monocytes. Mononuclear cells include monocytes, lymphocytes and a variable proportion of platelets, which are particularly difficult to remove by centrifugation of peripheral blood. Isolation by adsorption is based on the high adhesive properties of monocytes. It is expected that only monocytes will adhere to the surface, while other cellular elements will not. Therefore, monocytes should be easy to isolate by removing the non-adherent cells and washing the monolayer of adherent monocytes. In practice, however, a significant proportion of other cellular elements will also adhere to the surface (see FIG. 1 in ref. (22)).

The presence of other cellular elements during transformation of monocytes into dendritic cells can compromise the properties of the dendritic cells. Several previous studies have reported that immature dendritic cells generated in vitro lack immunocompetence (7, 8). Differences between immature DC produced in vitro and those found in vivo could arise from compromised differentiation of monocytes into DC in vitro. Differentiation could be compromised as a result of foreign body reactions that occur when monocytes and other cells present in a population of mononuclear cells contact plastic tissue culture surfaces (16, 17). Foreign body reactions can cause activation of mononuclear cells leading to production of factors that inhibit the ability of the monocytes to differentiate into fully competent immature dendritic cells.

Production of dendritic cells typically comprises plastic pre-treatment, adsorption and cultivation steps. In the method of the present invention, the process of adsorption of monocytes has been improved by decreasing adhesion of non-monocyte mononuclear cellular elements while retaining high adhesion of monocytes.

Non-specific adsorption of lymphocytes during the adsorption step of the preparation of dendritic cells is a common problem (22). In the present invention, pre-treatment of tissue culture plastic with a medium containing human serum (2-10%) is employed to coat plastic surfaces and decrease non-specific adsorption of lymphocytes. This effect of human serum is associated with the presence of fibronectin, since monocytes have receptors to fibronectin and are able to adhere to the surface-bound fibtonectin (28, 29). Use of human serum rather than fibronectin derived from another source is advantageous in the preparation of compositions for administration to immunotherapy patients.

A further decrease in non-specific adsorption and lymphocyte expansion is achieved in the present invention by inclusion of heparin in the plastic pre-treatment medium. Heparin is often used to decrease adsorption and activation of human blood cells during various types of extracorporeal blood processing (26). In these systems, covalent attachment of heparin to all surfaces used in extracorporeal devices and directly contacting with blood is employed. In generation of dendritic cells, heparin has been used as additive to the cultivation medium to prepare cells with high levels of expression of CD1a (27). In one aspect of the method of the present invention, however, heparin is used during the plastic pre-treatment step, particularly by inclusion of heparin in a tissue culture plastic pre-treatment medium.

The inventors have also found that adsorption and activation of platelets can be prevented if plasma is excluded from the sample medium during plastic pre-treatment, adsorption or cultivation. Addition of plasma to the culture medium is often used for preparation of dendritic cells (22, 23). Plasma comprises fibrinogen, which can mediate adsorption and activation of platelets (24), which are often present in a preparation of mononuclear cells.

In one aspect of the present invention, non-specific activation of monocytes is decreased during the adsorption step. Non-specific activation of monocytes usually promotes their differentiation into macrophages, compromising their differentiation into dendritic cells. In the present invention, a decrease in non-specific activation of monocytes is achieved by exclusion of adult human serum from the adsorption steps.

The methods described herein for generation of immature dendritic cells generate cells that are suitable for use as a dendritic cell vaccine. For example, immature dendritic cells produced according to the present invention can be injected directly into a tumour as part of an immunotherapy cancer treatment. The methods of the present invention also generate dendritic cells with an ability to induce strong antigen-specific CTL responses. When these immature dendritic cells are used as antigen presenting cells in in vitro immunization experiments, the responses generated have characteristics of memory-type responses, such as, expression by CTL of CD62L, specific recognition and killing of target cells and intensive proliferation after initial contact with target cells.

EXAMPLE 1

Preparation of Dendritic Cells

Dendritic cells were generated from buffy coats. 60 ml of buffy coat was diluted with 60 ml of Ca/Mg-free phosphate buffered saline (DPBS) (Cambrex), and applied on Lymphoprep (four 50-ml tubes each with 14 ml of the Lymphoprep). In order to minimize contamination of peripheral blood mononuclear cells (PBMCs) with platelets, the Lymphoprep centrifugation (200 g, 20° C.) was interrupted after 20 min according to procedure described by Romani et al., 1996 (25). The top 15-20 ml, containing most of the platelets, was transferred into 50-ml tubes and centrifugation was resumed (460 g, 20 min, 20° C.).

Coating of plastic tissue culture flasks was initiated by adding RPMI pre-treatment medium containing 5% of human AB serum to the flasks (T25). The pre-treatment medium was later removed from the T25 flasks and the flasks rinsed with 5 ml of RPMI 1640.

After termination of Lymphoprep centrifugation, mononuclear cells were harvested from the interface, diluted twice with cold EDTA-containing DPBS (Cambrex) and washed by 3 centrifugations, the first at 250 g, the second at 200 g and the last at 150 g. Centrifugation was carried out at 4° C. for 12 min. After the final centrifugation, cells were re-suspended in 30 ml of cold Ca/Mg-free DPBS and counted using Coulter Counter. The quantity of monocytes was estimated as the number of cells in a peak with average size around 9 p.m.

For the generation of dendritic cells, cell suspensions containing 4-8 Mio of monocytes per T25 polystyrene flask were transferred into centrifuge tubes and centrifuged at 250 g for 12 min at 4° C. 4 ml of AIM-V adsorption medium (with or without the addition of plasma and/or serum) was then added to each flask. After further centrifugation, the obtained pellet was re-suspended in the adsorption medium at a concentration of $4-8 \times 10^6$ monocytes/ml, and 1 ml of cell suspension was added to each T25 flask. After 30 min of adsorption at 37° C., non-adherent cells were removed, adherent cells were rinsed twice with warm RPMI 1640 medium and 5 ml of cultivation medium (AIM-V medium) was added to each flask. The flasks were placed into a $CO_2$-incubator at 37° C. Cytokines (GM-CSF, final concentration 100 ng/ml, and IL-4, final concentration 25 ng/ml) were added the next day and on day 3.

At day 4, the ability to mature was determined by addition the maturation cocktail consisting of: 10 ng/ml of TNF-alpha, 1000 U/ml of IL-6, 10 ng/ml of IL-1 and 0.1 µg/ml of prostaglandin E2. At day 6, the cells were harvested, their phenotype was determined by FACS analysis, and production of IL-12p70 in the supernatant was determined by ELISA analysis. Cells were stained with directly conjugated antibodies to CD83 (phycoerythrin (PE)) and CD86 (PE), all from Pharmingen, Becton Dickinson, Broendby, Denmark. Appropriate isotype controls were used. Samples were analysed using FC500 Flow Cytometer (Beckman Coulter).

The CD83 level of DC was used to indicate full maturation. To indicate absence of exhaustion, production of cytokine IL-12p70—that is considered to be important for Th1 polarization of immune response (19)—was measured. Absence of IL-12p70 production is considered to be a marker of exhausted mature dendritic cells (20, 21).

EXAMPLE 2

Effect of Plasma in the Adsorption Medium

Dendritic cell preparation as described in Example 1 was repeated with adsorption media comprising either: serum, plasma-derived serum or plasma, in addition to AIM-V medium.

The results of one of the experiments with cells from two donors are shown in FIG. 1. Plasma had a negative effect on the degree of maturation, while plasma-derived serum has smaller inhibitory effect. The negative effect of plasma-derived serum could be associated with incomplete removal of fibrinogen from plasma during clotting induced by addition of $CaCl_2$. In summary, plasma had a negative effect on the ability of the dendritic cells to reach full maturation.

EXAMPLE 3

Effect of Heparin in the Plastic Pre-Treatment Medium

Dendritic cells were prepared as described in Example 1. In the experiments of Example 3, heparin was added to the plastic pre-treatment medium so that plastic cell culture surfaces were coated with heparin during the pre-treatment step.

Figure 2:
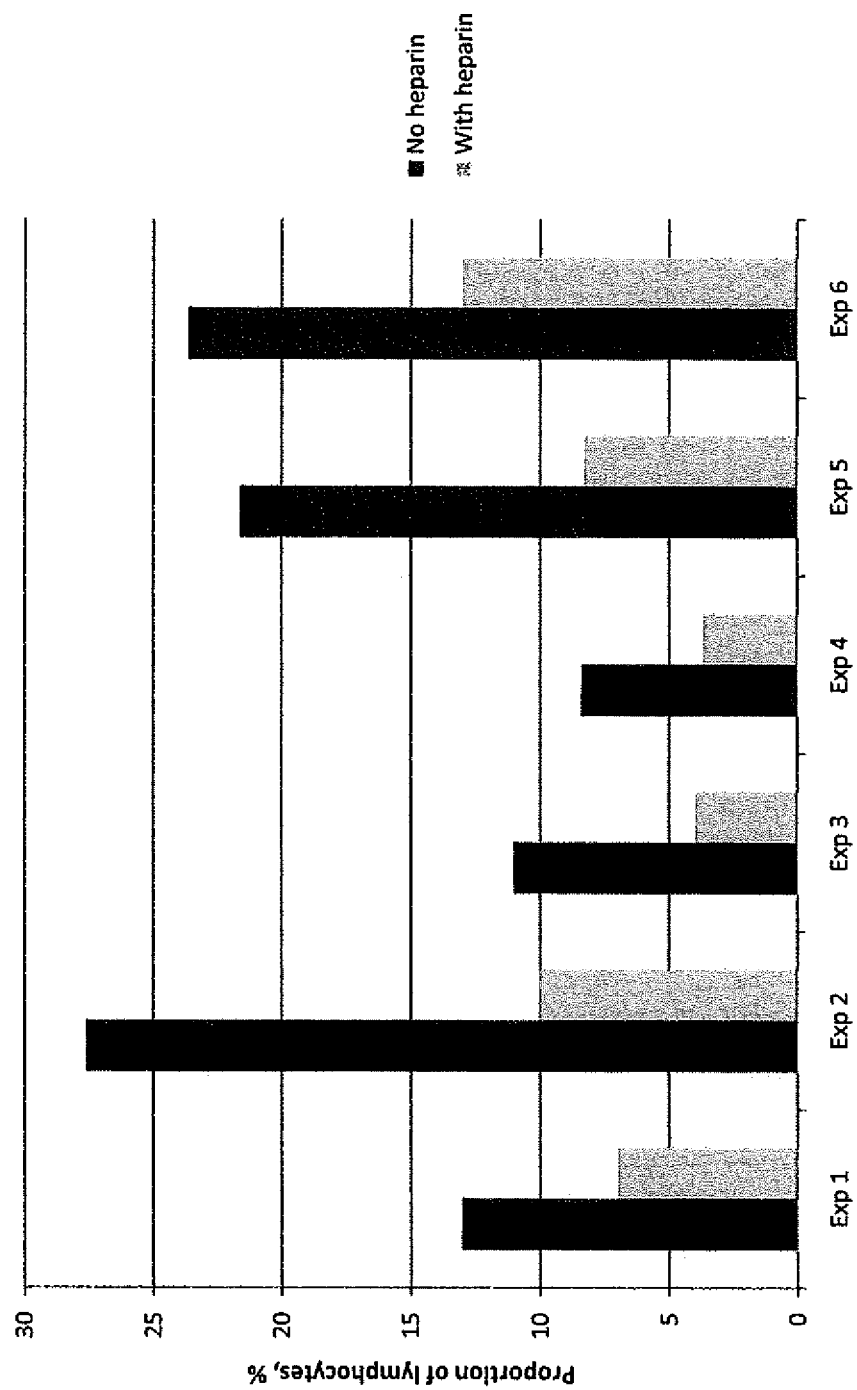
FIG. 2 illustrates the effect of inclusion of heparin in the pre-treatment medium on the proportion of lymphocytes in the final product.
Figure 3:
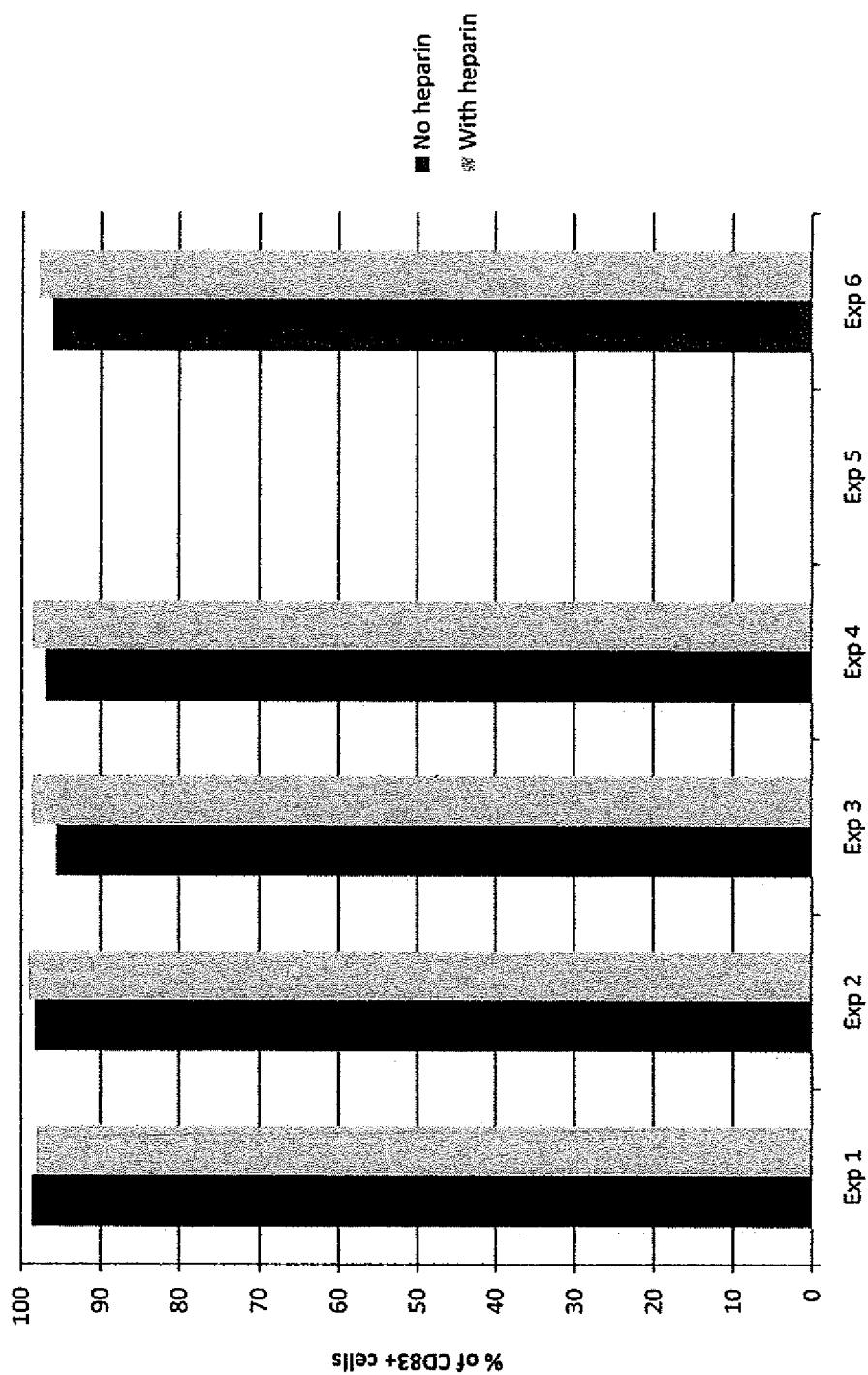
FIG. 3 illustrates the effect of inclusion of heparin in the pre-treatment medium on the phenotype of the mature dendritic cells generated.

The effect of heparin coating on the proportion of lymphocytes in the final product is demonstrated in FIG. 2. For the majority of donors, the proportion of lymphocytes decreased two-fold as a result of inclusion of heparin in the pre-treatment medium, while final yield of dendritic cells was either unchanged, or decreased insignificantly. Flow cytometry of the dendritic cells generated did not show changes in the levels of maturation of dendritic cells (FIG. 3).

For these dendritic cells the levels of IL-12p70 during maturation was also measured. Production of IL-12p70 was measured by sandwich ELISA that included capture Abs, standard or sample, biotinylated detection Abs, and HRP-streptavidin. Kit "DuoSet ELISA development System" for IL-12 p70 (R&D Systems) was used essentially according to the manufacturer's recommendations with some modifications. After overnight binding of capture antibodies to the Nunc maxisorp 96-well plates and washing, the blocking step was extended to at least 3 hrs at room temperature (r.t.). A standard curve was generated by seven serial dilutions of the standard, starting at 500 pg/ml. Standards and samples were incubated at r.t. for 2 hrs followed by incubation at 4° C. overnight. The subsequent steps were performed according to the manufacturer's protocol. Hydrogen peroxide-tetramethylbenzidine mixture was used as a substrate solution for HRP, and after terminating the enzymatic reaction, optical density was measured with wavelength correction as the difference between readings at 490 and 620 nm.

Figure 4:
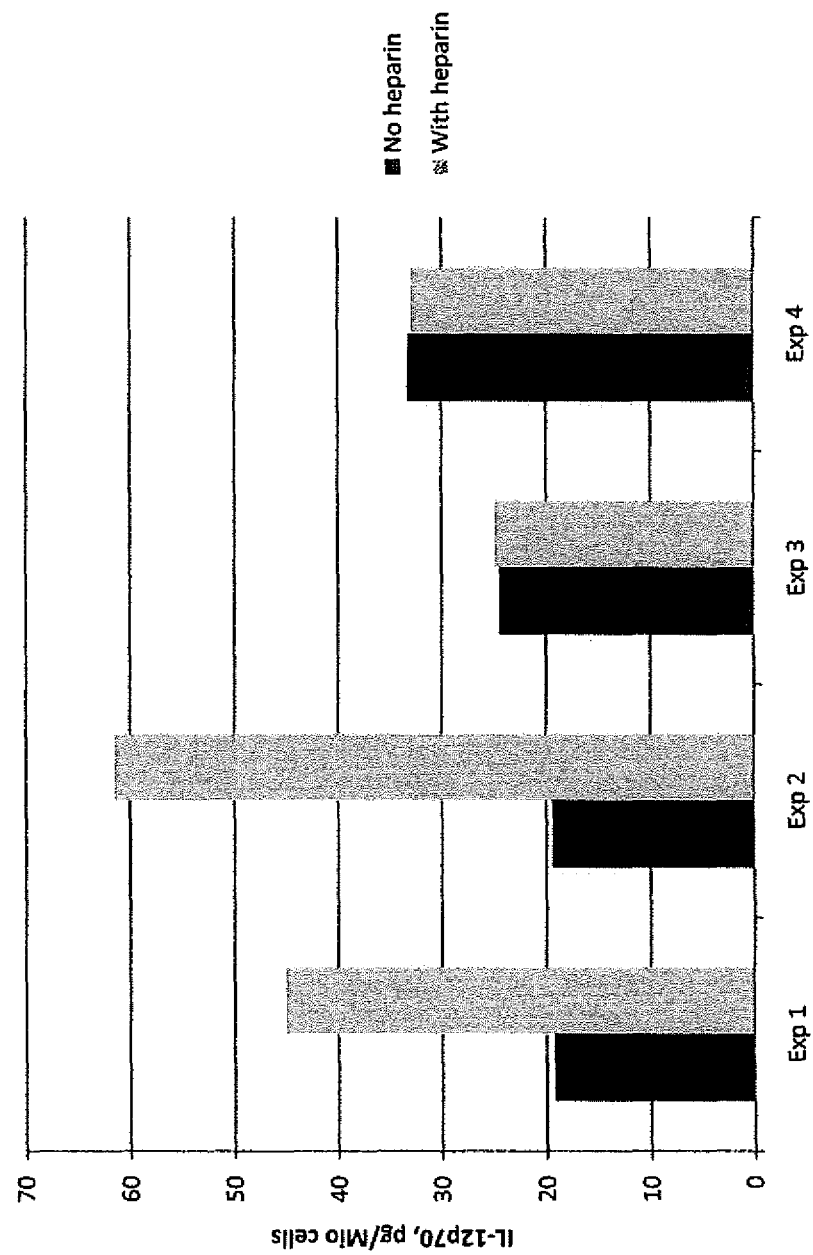
FIG. 4 illustrates the effect of inclusion of heparin in the pre-treatment medium on the production of IL-12p70 by the mature dendritic cells generated.

As illustrated in FIG. 4, the production of IL-12p70 by maturing dendritic cells was increased in several, but not all cultures.

In summary, inclusion of heparin in the plastic pre-treatment medium significantly decreases contamination of the final dendritic cells with lymphocytes without compromising the properties of the dendritic cells.

EXAMPLE 4

Effect of Human Serum in the Adsorption Medium

Figure 5:
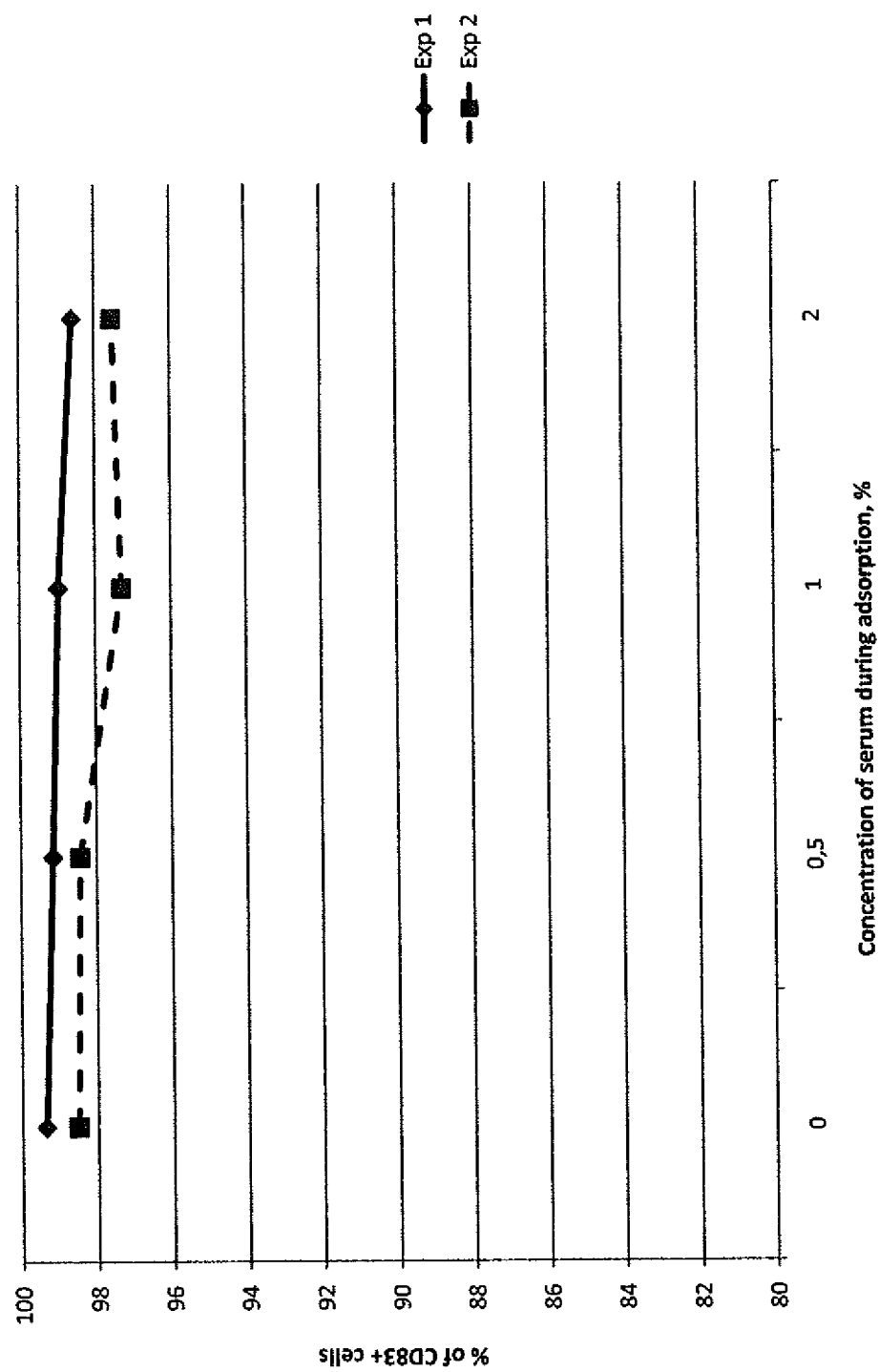
FIG. 5 illustrates the effect of inclusion of human serum in the adhesion medium on the phenotype of the mature dendritic cells generated.
Figure 6:
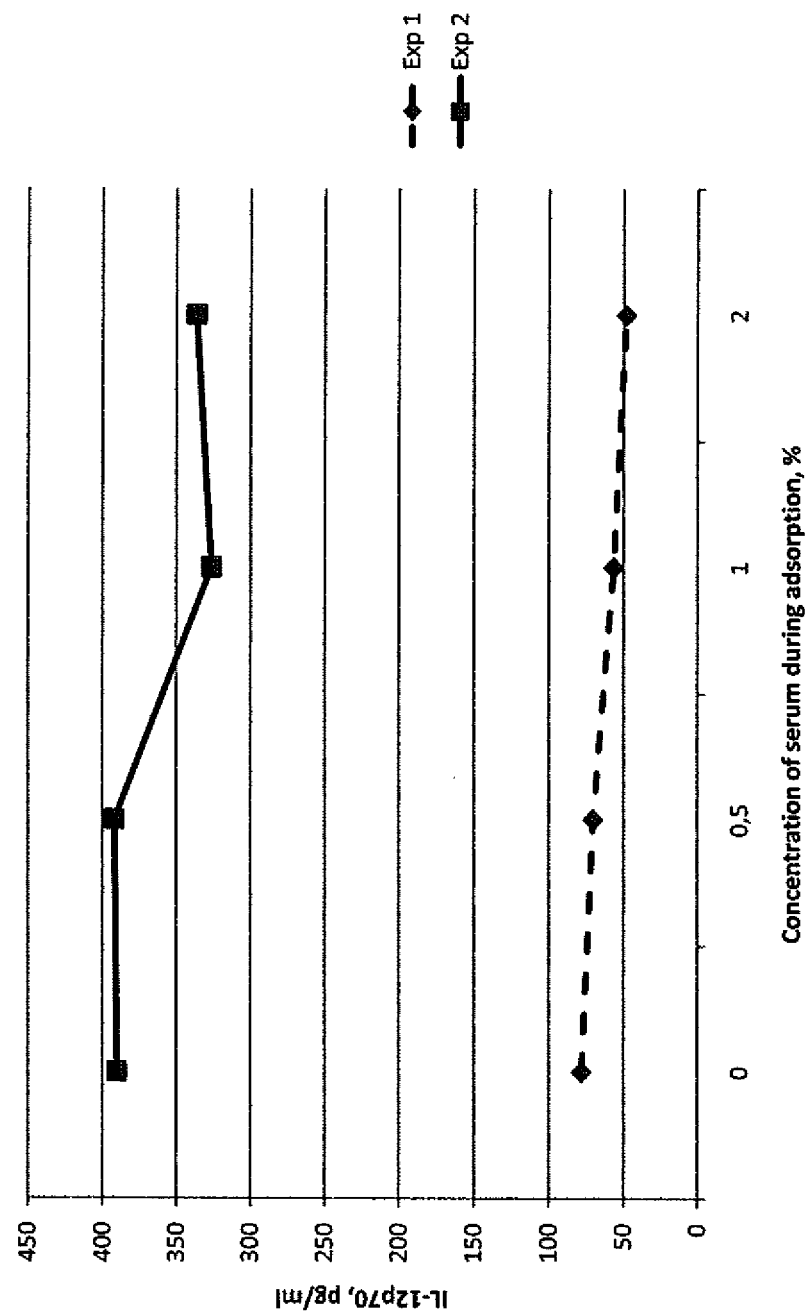
FIG. 6 illustrates the effect of inclusion of human serum in the adhesion medium on the production of IL-12p70 by the mature dendritic cells generated.

The method described in Example 1 was replicated with and without use of human serum in the adsorption medium and the properties of the resulting DC were investigated. FIGS. 5 and 6 illustrate the results obtained with cells from two donors. The presence of human serum during the adsorption step decreases the ability of dendritic cells to mature upon addition of the standard maturation cocktail, which is illustrated by the decrease in the proportion of CD83+ cells (FIG. 5) as well as by a decrease in the production of IL-12p70 (FIG. 6). This effect may be the result of presence of immunoglobulins in the serum that induce activation of monocytes (16).

EXAMPLE 5

Final Characterization of Dendritic Cells

Final characterization of immature dendritic cells was done using the following methods: FACS analysis for expression of the markers characteristic for immature dendritic cells present in vivo (CD1a and CD4), expression of IL-15, and uptake of labelled lysate.

Figure 7:
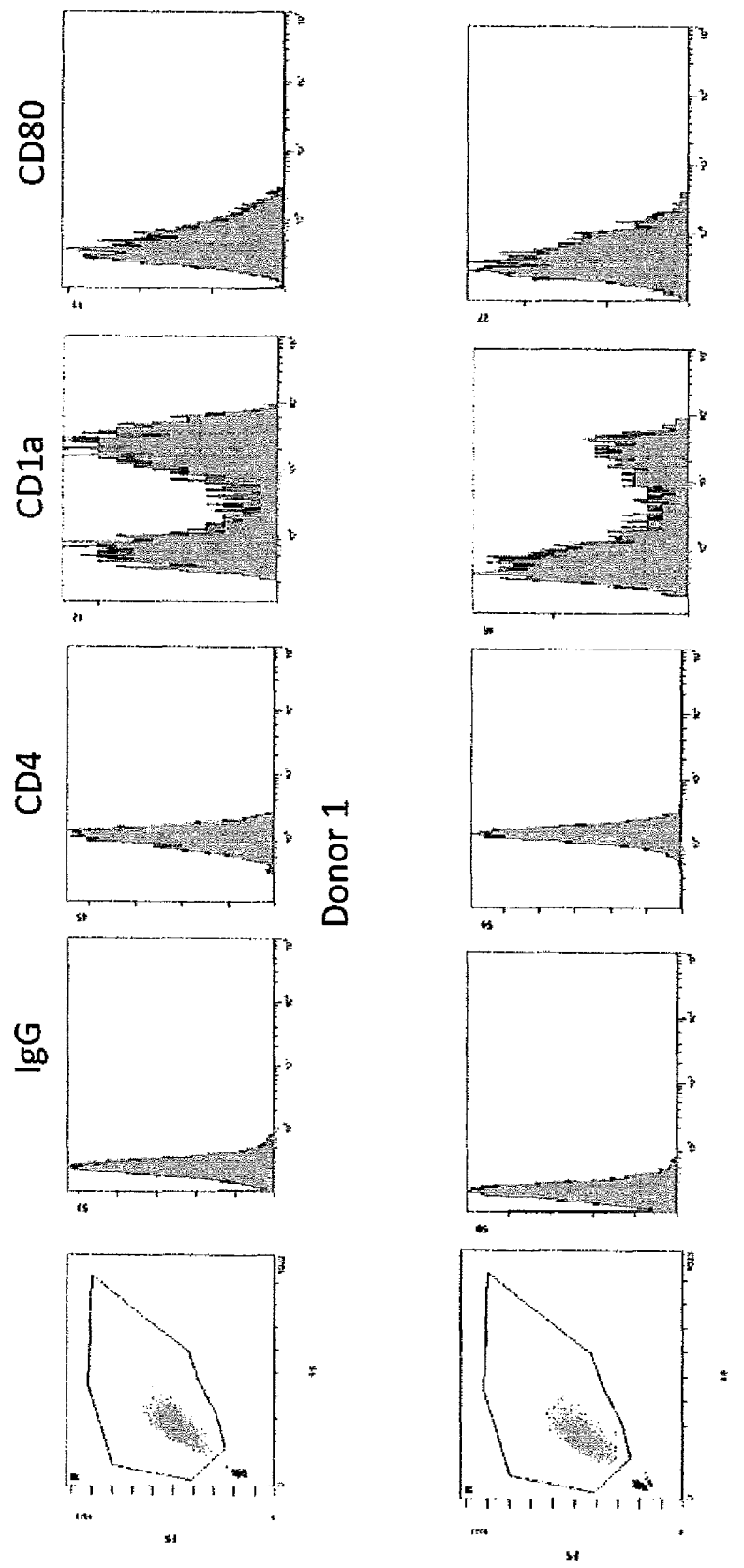
FIG. 7 illustrates the phenotype of immature dendritic cells.

The results from FACS analysis of immature dendritic cells are presented in FIG. 7. Cells were positive for CD1a and CD4. CD4 is a receptor for IL-16 produced by lymphocytes and for MHC class II. Interaction of CD4 on the surface of dendritic cells with ligands (MHC class II or IL-16) may induce activation of dendritic cells that can further increase their co-stimulatory function.

IL-15 was determined by two methods: mRNA expression by RT-PCR (conventional and real-time), and protein expression by sandwich ELISA.

Expression of mRNA for IL-15

RNA was isolated from the samples, stored in RNAlater (Ambion), DNase treated, reverse transcribed, and used in PCR. Preparations without reverse transcription were used as negative controls, in which the absence of PCR products indicated a complete lack of contaminating genomic DNA. Primers for human IL-15 are given in reference (30): TAAAACAGAAGCCAACTG (sense) and CAAGAAGT-GTTGATGAACAT (antisense). After initial denaturation at 95° C. for 5 min, samples were amplified in a DNA thermocycler for 35-38 cycles, each consisting of: denaturing for 60 seconds at 95° C., annealing for 60 seconds at 63° C. (cycle 1-3), 59° C. (cycle 4-6), and 56° C. (cycle 7-38) and extension for 45 seconds at 72° C., followed by a final extension at 72° C. for 10 min. Aliquots of PCR products were then electrophoresed on 2% agarose gel and visualized by ethidium bromide staining.

Real-time RT-PCR was performed using a Lightcycler Fastart DNA Master Plus SYBR green I and a Lightcycler 2.0 instrument (Roche Applied Science), primers and conditions were as in reference (31): sense—5'-GCCCTGGA-TATCTGTTCCAA-3', antisense—5'-GCTCGACA-CATTTCGTCTCA-3', resulting in a PCR product size 177 bp. Annealing was carried out at 61° C. Genes encoding β-actin and GAPDH were used as house-keeping gene controls.

Determination of IL-15 by ELISA

For IL-15 determination, 0.35 ml of each dendritic cell lysate was collected and kept frozen (−20° C.) until analysis. Concentrations of IL-15 were determined using "Ready-Set-Go" ELISA kit (eBioscience, San Diego, Calif., USA) combined with ELIST amplification system (PerkinElmer LAS, Inc.). The "Ready-Set-Go" kit included capture Abs, standard, biotinylated detection Abs, and HRP-streptavidin. The procedure was performed essentially according to the manufacturer's recommendations with the following modifications: 1) After overnight binding of capture antibodies to the Nunc Maxisorp 96-well plates and washing the plates, the blocking step was extended to at least 3 hrs at r.t.; 2) The standard curve was generated by seven serial dilutions of the standard, starting with 500 pg/ml of IL-15, and the standards and samples in triplicates were incubated at r.t. for 2 hrs followed by incubation at 4° C. overnight.

After binding of biotinylated detection Abs followed by HRP-streptavidin, amplification by ELIST was performed essentially according to the PerkinElmer's protocol. Then the enzymatic reaction of HRP was measured using tetramethylbenzidine (TMB) as a substrate. After terminating the reaction by sulfuric acid, optical density was measured with wavelength correction as the difference between readings at 450 and 550 nm.

Figure 8:
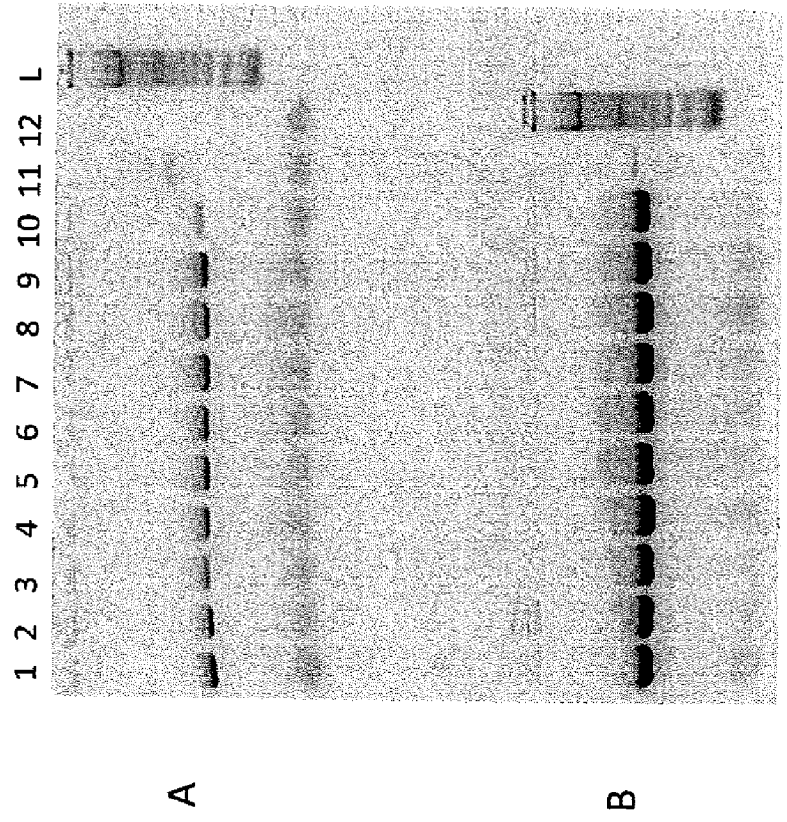
FIG. 8 illustrates expression of IL-15 in the immature dendritic cells.
Figure 9:
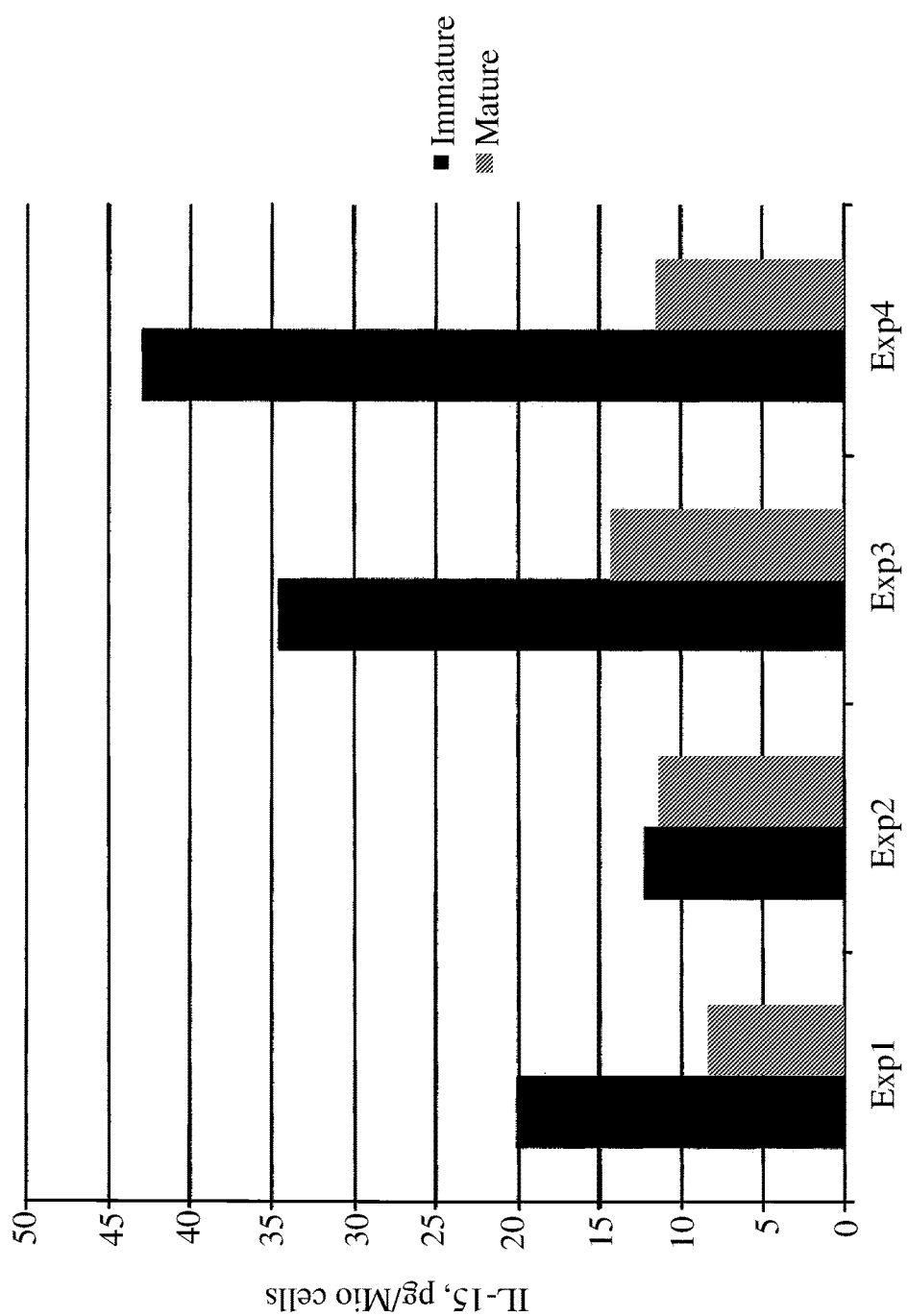
FIG. 9 illustrates detection of IL-15 protein in the lysates of immature and mature dendritic cells.

The results of determination of IL-15 are presented in FIG. 8 (RT-PCR analysis) and FIG. 9 (ELISA analysis). The results show that immature dendritic cells produced according to the present invention express mRNA for IL-15 and express the protein in the cells. It is of interest to note that upon maturation, the amount of IL-15 in the cells decreased in some experiments. Data from real-time PCR confirm the expression of mRNA for IL-15 (not shown). IL-15-expressing DC have been shown to be superior in induction of a CTL response compared to non-IL-15-producing cells (32, 33, 34). IL-15 is also able to drive generation and maintenance of memory CD8+ cells (35, 36). Therefore, IL-15 expression may reflect the high competence of the dendritic cells generated by the present method for inducing memory type CTL responses.

To demonstrate the ability of the generated dendritic cells to take up lysate from tumour cells, the lysate—made as described in the Example 6—was labeled using the following procedure. The tumour cell lysate (2-4 mg protein/ml) was prepared in DPBS with Ca/Mg, 1M NaOH was added to raise pH to 9.0. 3 mg of N-Hydroxysuccinimide-Fluorescein (NHS-Fluorescein, Pierce) was dissolved in 50 µl dry DMSO, and added to the lysate. The mixture was incubated at 37° C. for 1.5 hr in the dark. The modified lysate was dialyzed, with 1.5 l DPBS (without Ca/Mg) being replaced at 12 hr intervals, until no fluorescence is detected in the dialysate under UV, 254 nm. 1.5 µl of the final lysate and NHS-Fluorescein solution were spotted on a TLC plate with a fluorescent indicator (Kieselgel 60 $F_{254}$, Merck) and developed in a chromatographic system acetonitryl:$H_2O$/4:1. The plate was viewed under UV 254 nm in order to ensure that all label in the lysate was covalently attached to the protein and that the lysate did not contain free label.

FIG. 10 demonstrates microscopy of dendritic cells incubated for 60 minutes with the labelled lysate at 37° C. (a—light microscopy; b—fluorescent microscopy). It can clearly be seen that all the dendritic cells demonstrate intensive uptake of the labelled lysate.

In summary, the dendritic cells generated by the described method, are highly homogeneous, they express the required set of surface molecules characteristic for dendritic cells present in vivo, they express IL-15 and they have high ability to uptake exogenously added lysate of tumour cells.

EXAMPLE 6

Immature Dendritic Cells Loaded with Lysate from a Tumour Cell Line Stimulate In Vitro Generation of a Tumour-Specific CTL Response with the Characteristics of a Memory-Type Response The ability of dendritic cells, prepared by the method of the present invention and loaded with tumour antigens, to stimulate the generation of an anti-tumour CTL response was tested in vitro using lysate of breast cancer cell line MDA-MB-231 as a source of tumour antigens. This cell line expresses broad spectrum cancer/testis antigens (see WO 2008/081035).

Tumour cells were cultured in RPMI 1640 medium supplemented with L-glutamine and 10% of fetal calf serum. For preparation of lysate, cells were harvested by trypsinization, washed, counted, suspended in RPMI 1640 medium at a concentration of $10^7$/ml and subjected to 5 cycles of freezing (liquid nitrogen) and thawing (water bath, 37° C.). The resultant lysate was clarified by centrifugation (3000 g, 60 min, 4° C.) and stored in aliquots at −80° C.

Dendritic cells were prepared as described in Example 1. At day 4 or 5, 10% of tumour lysate was added to the culture of the dendritic cells for loading the dendritic cells with tumour lysate.

After overnight incubation, cells were harvested, washed, re-suspended in lymphocyte cultivation medium (AIM-V with addition of 5% of autologous serum). For in vitro generation of a tumour-specific CTL responses the loaded dendritic cells were mixed with autologous non-adherent lymphocytes at 1:40 ratio and placed into 24-well plates, 2 Mio of the lymphocytes per well. At days 2, 5 and 8, half of medium was removed and 1 ml of fresh medium containing 50 U/ml of IL-2 was added into each well. At day 10 or 11, the cells were harvested, and the concentration of large activated lymphocytes was determined using Coulter Counter. The cells were then washed, mixed with thawed lysate-loaded dendritic cells at a ratio of 10:1 and placed into the wells of 24-well plates ($0.5 \times 10^6$ lymphocytes per well), in 2 ml of lymphocyte culture medium.

At days 2 and 5, half of the medium was removed and 1 ml of fresh medium containing 50 U/ml of IL-2 was added into each well. At day 7, cells were harvested, counted, and used for FACS analysis and for testing for cytotoxicity against a panel of tumour cell lines.

Figure 11:
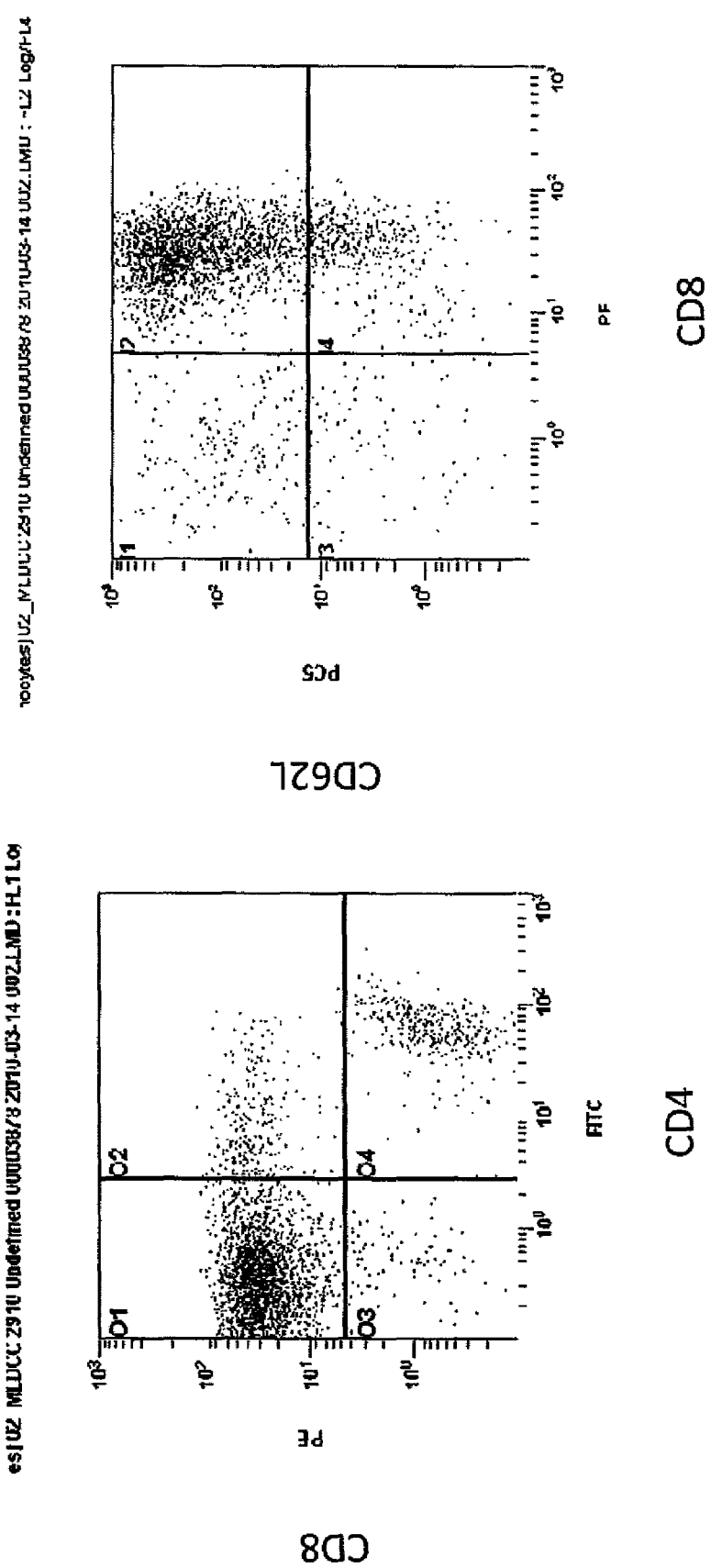
FIG. 11 illustrates the phenotype of lymphocytes stimulated two times with dendritic cells loaded with lysate of breast cancer cell line MDA-MB-231.

Phenotypic analysis of lymphocytes generated in one of several experiments is demonstrated in FIG. 11. As can be seen, a significant portion of the cells are CD8+ T lymphocytes and the majority of them express high levels of CD62L.

Cytotoxic activity of the activated lymphocytes was determined morphologically for HLA-A2-positive donors, using a panel of tumour cell lines: breast cancer cell lines MCF-7 (HLA-A2+), MDA-MB-231 (HLA-A2+) and T47D (HLA-A2−), prostate cancer cell line LNCaP (HLA-A2+). $5 \times 10^4$ tumour cells were seeded in 24-well plates in 1 ml of RPMI-1640 medium with addition of 10% of FCS and incubated for 2 days before testing. 1 ml of the suspension of the isolated lymphocytes containing $1 \times 10^6$ cells was added to the tumour cells.

Lytic activity of lymphocytes was detected morphologically after 24-48 hours of incubation. The results of such experiments are shown in the FIGS. 12 and 13. As could be seen, significant lysis was seen with all HLA-A2-positive tumour cell lines, while HLA-A2-negative T47D tumour cells were resistant to lysis. Intensive proliferation of lymphocytes is seen in cultures with HLA-A2-positive tumour cells, while no proliferation is seen in the culture with the resistant HLA-A2-negative T47D cell line.

These findings—high level of expression of CD62L, lysis of only HLA-A2+ tumour cell lines, and intensive proliferation of lymphocytes after contact with, and recognition of, the appropriate tumour antigens—point to generation of specific memory type CTL response in the system of the present invention.

In summary, the improved method of the present invention for generating DC results in fully immunocompetent immature dendritic cells able to stimulate a specific memory-type antitumour T cell response.

REFERENCES

1. Banchereau, J., F. Briere, C. Caux, J. Davoust, S. Lebecque, Y. J. Liu, B. Pulendran, and K. Palucka. 2000. Immunobiology of dendritic cells. *Annu. Rev. Immunol.* 18:767.
2. Banchereau, J., and A. K. Palucka. 2005. Dendritic cells as therapeutic vaccines against cancer. *Nat. Rev. Immunol.* 5:296.
3. Peters, J. H., S. Ruhl, and D. Friedrichs. 1987. Veiled accessory cells deduced from monocytes. *Immunobiology* 176:154.
4. Peters, J. H., H. Xu, J. Ruppert, D. Ostermeier, D. Friedrichs, and R. K. Gieseler. 1993. Signals required for differentiating dendritic cells from human monocytes in vitro. *Adv. Exp. Med. Biol.* 329:275.

5. Romani, N., S. Gruner, D. Brang, E. Kämpgen, A. Lenz, B. Trockenbacher, G. Konwalinka, P. O. Fritsch, R. M. Steinman, and G. Schuler. 1994. Proliferating dendritic cell progenitors in human blood. *J. Exp. Med.* 180:83.
6. Sallusto, F., and A. Lanzavecchia. 1994. Efficient presentation of soluble antigen by cultured human dendritic cells is maintained by granulocyte/macrophage colony-stimulating factor plus interleukin 4 and downregulated by tumour necrosis factor. *J. Exp. Med.* 179:1109.
7. Mahnke, K., E. Schmitt, L. Bonifaz, A. H. Enk, and H. Jonuleit. 2002. Immature, but not inactive: the tolerogenic function of immature dendritic cells. *Immunol. Cell Biol.* 80:477.
8. Steinman, R. M., and M. C. Nussenzweig. 2002. Avoiding horror autotoxicus: the importance of dendritic cells in peripheral T cell tolerance. *Proc. Natl. Acad. Sci. U.S.A* 99:351.
9. Nestle, F. O., S. Alijagic, M. Gilliet, Y. Sun, S. Grabbe, R. Dummer, G. Burg, and D. Schadendorf. 1998. Vaccination of melanoma patients with peptide- or tumour lysate-pulsed dendritic cells. *Nature (Med.)* 4:328.
10. Mackensen, A., R. Drager, M. Schlesier, R. Mertelsmann, and A. Lindemann. 2000. Presence of IgE antibodies to bovine serum albumin in a patient developing anaphylaxis after vaccination with human peptide-pulsed dendritic cells. *Cancer Immunol. Immunother.* 49:152.
11. Engell-Noerregaard, L., T. H. Hansen, M. H. Andersen, S. P. Thor, and I. M. Svane. 2009. Review of clinical studies on dendritic cell-based vaccination of patients with malignant melanoma: assessment of correlation between clinical response and vaccine parameters. *Cancer Immunol. Immunother.* 58:1.
12. Dumortier, H., G. J. van Mierlo, D. Egan, W. van Ewijk, R. E. Toes, R. Offringa, and C. J. Melief. 2005. Antigen presentation by an immature myeloid dendritic cell line does not cause CTL deletion in vivo, but generates CD8+ central memory-like T cells that can be rescued for full effector function. *J. Immunol.* 175:855.
13. Sallusto, F., J. Geginat, and A. Lanzavecchia. 2004. Central memory and effector memory T cell subsets: function, generation, and maintenance. *Annu. Rev. Immunol.* 22:745.
14. Klebanoff, C. A., L. Gattinoni, and N. P. Restifo. 2006. CD8 T-cell memory in tumour immunology and immunotherapy. *Immunol. Rev.* 211:214.
15. Klebanoff, C. A., L. Gattinoni, P. Torabi-Parizi, K. Kerstann, A. R. Cardones, S. E. Finkelstein, D. C. Palmer, P. A. Antony, S. T. Hwang, S. A. Rosenberg, T. A. Waldmann, and N. P. Restifo. 2005. Central memory self/tumour-reactive CD8+ T cells confer superior antitumour immunity compared with effector memory T cells. *Proc. Natl. Acad. Sci. U.S.A.* 102:9571.
16. Shen, M., I. Garcia, R. V. Maier, and T. A. Horbett. 2004. Effects of adsorbed proteins and surface chemistry on foreign body giant cell formation, tumour necrosis factor alpha release and procoagulant activity of monocytes. *J. Biomed. Mater. Res.* 70A:533.
17. Shen, M., and T. A. Horbett. 2001. The effects of surface chemistry and adsorbed proteins on monocyte/macrophage adhesion to chemically modified polystyrene surfaces. *J. Biomed. Mater. Res.* 57:336.
18. Zhou, L. J., and T. F. Tedder. 1995. Human blood dendritic cells selectively express CD83, a member of the immunoglobulin superfamily. *J. Immunol.* 154:3821.
19. Heufler, C., F. Koch, U. Stanzl, G. Topar, M. Wysocka, G. Trinchieri, A. Enk, R. M. Steinman, N. Romani, and G. Schuler. 1996. Interleukin-12 is produced by dendritic cells and mediates T helper 1 development as well as interferon-gamma production by T helper 1 cells. *Eur. J. Immunol.* 26:659.
20. Kalinski, P., C. M. Hilkens, A. Snijders, F. G. Snijdewint, and M. L. Kapsenberg. 1997. IL-12-deficient dendritic cells, generated in the presence of prostaglandin E2, promote type 2 cytokine production in maturing human naive T helper cells. *J. Immunol.* 159:28.
21. Mailliard, R. B., A. Wankowicz-Kalinska, Q. Cai, A. Wesa, C. M. Hilkens, M. L. Kapsenberg, J. M. Kirkwood, W. J. Storkus, and P. Kalinski. 2004.-type-1 polarized dendritic cells: A novel immunization tool with optimized CTL-inducing activity. *Cancer Res.* 64:5934.
22. Thurner, B., C. Roder, D. Dieckmann, M. Heuer, M. Kruse, A. Glaser, P. Keikavoussi, E. Kämpgen, A. Bender, and G. Schuler. 1999. Generation of large numbers of fully mature and stable dendritic cells from leukapheresis products for clinical application. *J. Immunol. Methods* 223:1.
23. Jonuleit, H., U. Kuhn, G. Muller, K. Steinbrink, L. Paragnik, E. Schmitt, J. Knop, and A. H. Enk. 1997. Pro-inflammatory cytokines and prostaglandins induce maturation of potent immunostimulatory dendritic cells under fetal calf serum-free conditions. *Eur. J. Immunol.* 27:3135.
24. Tsai, W. B., J. M. Grunkemeier, C. D. McFarland, and T. A. Horbett. 2002. Platelet adhesion to polystyrene-based surfaces preadsorbed with plasmas selectively depleted in fibrinogen, fibronectin, vitronectin, or von Willebrand's factor. *J. Biomed. Mater. Res.* 60:348.
25. Romani, N., D. Reider, M. Heuer, S. Ebner, E. Kämpgen, B. Eibl, D. Niederwieser, and G. Schuler. 1996. Generation of mature dendritic cells from human blood. An improved method with special regard to clinical applicability. *J. Immunol. Methods* 196:137.
26. Wendel, H. P., and G. Ziemer. 1999. Coating-techniques to improve the hemocompatibility of artificial devices used for extracorporeal circulation. *Eur. J. Cardiothorac. Surg.* 16:342.
27. Xia, C. Q., and K. J. Kao. 2002. Heparin induces differentiation of $CD1a^+$ dendritic cells from monocytes: phenotypic and functional characterization. *J. Immunol.* 168:1131.
28. Bevilacqua, M. P., D. Amrani, M. W. Mosesson, and C. Bianco. 1981. Receptors for cold-insoluble globulin (plasma fibronectin) on human monocytes. *J. Exp. Med.* 153:42.
29. Owen, C. A., E. J. Campbell, and R. A. Stockley. 1992. Monocyte adherence to fibronectin: role of CD11/CD18 integrins and relationship to other monocyte functions. *J. Leukoc. Biol.* 51:400.
30. Tinhofer, I., I. Marschitz, T. Henn, A. Egle, and R. Greil. 2000. Expression of functional interleukin-15 receptor and autocrine production of interleukin-15 as mechanisms of tumour propagation in multiple myeloma. *Blood* 95:610.
31. Franchi, A., J. Zaret, X. Zhang, S. Bocca, and S. Oehninger. 2008. Expression of immunomodulatory genes, their protein products and specific ligands/receptors during the window of implantation in the human endometrium. *Mol. Hum. Reprod.* 14:413.
32. Ratzinger, G., J. Baggers, M. A. De Cos, J. Yuan, T. Dao, J. L. Reagan, C. Munz, G. Heller, and J. W. Young. 2004. Mature human Langerhans cells derived from CD34+ hematopoietic progenitors stimulate greater cytolytic T lymphocyte activity in the absence of bioactive IL-12p70, by either single peptide presentation or cross-priming, than do dermal-interstitial or monocyte-derived dendritic cells. *J. Immunol.* 173:2780.
33. Klechevsky, E., R. Morita, M. Liu, Y. Cao, S. Coquery, L. Thompson-Snipes, F. Briere, D. Chaussabel, G. Zurawski, A. K. Palucka, Y. Reiter, J. Banchereau, and H. Ueno. 2008. Functional specializations of human epidermal langerhans cells and CD14+ dermal dendritic cells. *Immunity.* 29:497.
34. Palucka, K., H. Ueno, G. Zurawski, J. Fay, and J. Banchereau. 2010. Building on dendritic cell subsets to improve cancer vaccines. *Curr. Opin. Immunol.*
35. Schluns, K. S., K. Williams, A. Ma, X. X. Zheng, and L. Lefrancois. 2002. Cutting edge: requirement for IL-15 in the generation of primary and memory antigen-specific CD8 T cells. *J. Immunol.* 168:4827.
36. Becker, T. C., E. J. Wherry, D. Boone, K. Murali-Krishna, R. Antia, A. Ma, and R. Ahmed. 2002. Interleukin 15 is required for proliferative renewal of virus-specific memory CD8 T cells. *J. Exp. Med.* 195:1541.

The invention claimed is:

1. A method of producing immature dendritic cells by cultivation of monocytes, the method comprising:
pre-treatment of a tissue culture surface with a pre-treatment medium comprising heparin and human serum;
adsorption of monocytes using an adsorption medium that is both plasma-free and serum-free; and
cultivation of monocytes using a cultivation medium.

2. A method as claimed in claim 1 wherein the human serum has a concentration of between 2 and 10%.

3. A method as claimed in claim 1 wherein the pre-treatment medium has a heparin concentration of between 10 and 200 U/ml.

4. A method as claimed in claim 3 wherein the pre-treatment medium has a heparin concentration of between 25 and 100 U/ml.

5. A composition comprising immature dendritic cells produced by a method including:
pre-treatment of a tissue culture surface with a pre-treatment medium comprising heparin, and human serum;
adsorption of monocytes using an adsorption medium that is both plasma-free and serum-free; and
cultivation of monocytes using a cultivation medium, wherein the source of monocytes is centrifuged peripheral blood that comprises other mononuclear cells, and the ratio of monocytes compared to other mononuclear cells that are adsorbed is higher than the ratio obtained using a pre-treatment medium that does not contain either human serum or heparin or both.

6. A composition as claimed in claim 5, which is a pharmaceutical composition.

7. A composition as claimed in claim 6, which is a pharmaceutical composition for the treatment of cancer by immunotherapy.

8. A composition as claimed in claim 7, which is injectable directly into a tumour.

9. An antigen-presenting composition produced from a composition comprising immature dendritic cells according to claim 5.

10. An antigen-presenting composition as claimed in claim 9, which is a pharmaceutical composition for the treatment of cancer by stimulating an immune response against tumours.

11. A method of treating cancer by administering an antigen-presenting composition comprising immature dendritic cells produced in accordance with the method of claim 1.

12. A method for treating cancer wherein the composition as claimed in claim 5 is injected directly into a tumour.

13. A method of treating cancer by stimulating an immune response against tumours, comprising administering an antigen-presenting composition according to claim 9 to a cancer patient to stimulate an immune response to the tumour antigens.

14. A method of preparing a cytotoxic composition, comprising loading immature dendritic cells in a composition according to claim 5 with tumour antigens to produce antigen-presenting dendritic cells, and mixing the antigen-presenting dendritic cells with T lymphocytes to activate the T lymphocytes, thereby obtaining a cytotoxic composition containing tumour-specific CD8+ cytotoxic T lymphocytes.

15. A method of treating cancer by adoptive T cell therapy, comprising preparing a cytotoxic composition in accordance with the method of claim 14, and administering the cytotoxic composition to a cancer patient.

* * * * *